US011020496B2

(12) United States Patent
Willenberg et al.

(10) Patent No.: US 11,020,496 B2
(45) Date of Patent: Jun. 1, 2021

(54) COMPOSITIONS FOR NEUROMODULATION OF MOSQUITO FEEDING BEHAVIOR AND USES THEREOF

(71) Applicant: University of Central Florida Research Foundation, Inc., Orlando, FL (US)

(72) Inventors: Bradley Jay Willenberg, Orlando, FL (US); Sudipta Seal, Orlando, FL (US); Alexander John Bosak, Orlando, FL (US); Alicia Renae Willenberg, Saint Cloud, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 215 days.

(21) Appl. No.: 16/127,587

(22) Filed: Sep. 11, 2018

(65) Prior Publication Data

US 2019/0076556 A1 Mar. 14, 2019

Related U.S. Application Data

(60) Provisional application No. 62/585,707, filed on Nov. 14, 2017, provisional application No. 62/556,643, filed on Sep. 11, 2017.

(51) Int. Cl.

| | |
|---|---|
| ***A61K 49/00*** | (2006.01) |
| ***A61K 31/4168*** | (2006.01) |
| ***A61K 31/137*** | (2006.01) |
| ***A23K 20/163*** | (2016.01) |
| ***A61K 31/11*** | (2006.01) |
| ***A61K 38/08*** | (2019.01) |
| ***A23K 50/90*** | (2016.01) |
| ***A61K 31/135*** | (2006.01) |

(52) U.S. Cl.

CPC ........ *A61K 49/0093* (2013.01); *A23K 20/163* (2016.05); *A23K 50/90* (2016.05); *A61K 31/11* (2013.01); *A61K 31/135* (2013.01); *A61K 31/137* (2013.01); *A61K 31/4168* (2013.01); *A61K 38/08* (2013.01); *A61K 49/0004* (2013.01); *A61K 49/0008* (2013.01)

(58) Field of Classification Search

CPC ............ A61K 49/0093; A61K 49/0008; A61K 49/0004; A61K 31/4168; A61K 31/137; A61K 31/11; A61K 38/08; A61K 31/135; A23K 20/163; A23K 50/90

See application file for complete search history.

(56) References Cited

U.S. PATENT DOCUMENTS

| | | | | |
|---|---|---|---|---|
| 4,678,775 A * | 7/1987 | Nathanson | ............. | A01N 33/04 514/183 |
| 5,935,953 A * | 8/1999 | Kuhar | ..................... | A61P 25/00 514/235.2 |
| 2014/0200337 A1* | 7/2014 | Bruno | ................. | C12N 15/115 536/23.1 |
| 2015/0020439 A1 | 1/2015 | Willenberg et al. | | |

FOREIGN PATENT DOCUMENTS

| | | | |
|---|---|---|---|
| WO | WO-2014035993 A2 * | 3/2014 | ....... G01N 33/56966 |
| WO | 2017027677 | 2/2017 | |

OTHER PUBLICATIONS

Agnihotri NP, Bhide M. Design of Aptamer-Gold Nanoparticles Based Colorimetric Assay for the Early Diagnosis of Breast Tumor. International Journal of Science and Research, 2012, 1703-1707.
Al-Anzi, B. et al. The Leucokinin Pathway and its Neurons Regulate Meal Size in *Drosophila*. Curr Biol. 2010. 20(11): 969-978. doi:10.1016.
Bryant, JM., Torosdag, S., Schvartz, N., Lucian, F., Fertig, H., Schwartz, S., Quan, RBF. Antihypertensive Properties of Pargyline Hydrochloride. J. A. M. A., 1961, 178:406-9.
Calvo, E.; Mans, B. J.; Andersen, J. F.; Ribeiro, J. M. C., Function and evolution of a mosquito salivary protein family. Journal of Biological Chemistry 2006, 281 (4), 1935-1942.
Castelli, MV., Lodeyro, AF., Malheiros, A., Zacchino, SAS., Roveri, OA. Inhibition of the Mitochondrial ATP synthesis by Polygodial, a Naturally Occurring Dialdehyde Unsaturated Sesquiterpene. Biochemical Pharmacology. 2005. 70 82-89.
Cheung Y. Development of aptamer-nanoparticle conjugates as a new approach to malaria diagnosis: University of Hong Kong; 2012.
Choo YM, Buss GK, Tan K, Leal WS Multitasking roles of Mosquito labrum in oviposition and blood feeding. Front.Physiol 2015, 6:306. doi:10.3389/fphys.2015.00306.
Corfas R., Vosshall L. The Cation Channel TRPA1 Tunes Mosquito Thermotaxis to Host Temperatures, eLife (2015) 4:e11750.
Das, S.; Singh, S.; Dowding, J. M.; Oommen, S.; Kumar, A.; Sayle, T. X. T.; Saraf, S.; Patra, C. R.; Vlahakis, N. E.; Sayle, D. C.; Self, W. T.; Seal, S., The induction of angiogenesis by cerium oxide nanoparticles through the modulation of oxygen in intracellular environments. Biomaterials 2012, 33 (31), 7746-7755.
Dolzer, J., Krannich, S., Fischer, K., Stengl, M. Oscillations of the Transepithelial Potential of Moth Olfactory Sensilla are Influenced by Octopamine and Serotonin. The Journal of Experimental Biology 2001. 204, 2781-2794.
El-Kholy, S., Stephano, F., Li, Y., Bhandari, A., Fink, C., Roeder, T. Expression analysis of octopamine and tyramine receptors in *Drosophila*. Cell Tissue Res. 2015. 361:669-684.

(Continued)

*Primary Examiner* — Robert S Cabral
(74) *Attorney, Agent, or Firm* — Meunier Carlin & Curfman LLC

(57) ABSTRACT

The present disclosure relates to compositions and methods for enhancing mosquito feeding.

17 Claims, 3 Drawing Sheets

(56) References Cited

OTHER PUBLICATIONS

Ellington, A. D. & Szostak, J. W. In vitro selection of RNA molecules that bind specific ligands. Nature 346, 818-822 (1990).
Farooqui, T., Robinson, K., Vaessin, H., Smith, B. Modulation of Early Olfactory Processing by an Octopaminergic Reinforcement Pathway in the Honeybee. The Journal of Neuroscience, 2003. 23(12):5370-5380.
Fox, M., French, H., LaPorte, J., Blackler, A., Murphy, D. The Serotonin 5-HT2A Receptor Agonist TCB-2: A Behavioral and Neurophysiological Analysis. Psychopharmacology. 2010. 212:13-23.
Franz, A., Kantor, A., Passarelli, A. L., Clem, R. Tissue Barriers to Arbovirus Infection in Mosquitoes. Viruses 2015, 7, 3741-3767.
Gasque, G., Conway, S., Huang, J., Rao, Y., Vosshall, L. Small Molecule Drug Screening in *Drosophila* Identifies the 5HT2A Receptor as a Feeding Modulation Target. Scientific Reports. 2013. DOI: 10.1038/srep02120.
Gwadz, R. Regulation of Blood Meal Size in the Mosquito. J. Insect Physiol., 1969, vol. 15, 7 pages.
Hall-Mendelin, S.; Ritchie, S. A.; Johansen, C. A.; Zborowski, P.; Cortis, G.; Dandridge, S.; Hall, R. A.; van den Hurk, A. F., Exploiting mosquito sugar feeding to detect mosquito-borne pathogens. Proceedings of the National Academy of Sciences of the United States of America 2010, 107 (25), 11255-11259.
Harrington, L., Edman, J., Scott, T. Why Do Female Aedes aegypti (Diptera: Culicidae) Feed Preferentially and Frequently on Human Blood? Journal of Medical Entomology 2001, 38(3):411-422.
http://www.who.int/mediacentre/factsheets/fs117/en/ as of Apr. 5, 2017, 8 pages.
https://www.cdc.gov/zika/geo/united-states.html as of Mar. 30, 2017, 5 pages.
Jeon, W.; Lee, S.; Manjunatha, D. H.; Ban, C., A colorimetric aptasensor for the diagnosis of malaria based on cationic polymers and gold nanoparticles. Analytical Biochemistry 2013, 439 (1), 11-16.
Jung et al. A novel olfactory pathway is essential for fast and efficient blood-feeding in mosquitoes. Scientific Reports 2015, 5:13444.
Kwona, H., Ali Aghab, M., Smith, R., Nachmand, R., Marion-Pollb, F., Pietrantonioa, P. Leucokinin Mimetic Elicits Aversive Behavior in Mosquito *Aedes aegypti* (L.) and Inhibits the Sugar Taste Neuron. P Natl Acad Sci. 2016, 6880-6885. DOI: 10.1073.
Lee, S.; Manjunatha, D. H.; Jeon, W.; Ban, C., Cationic Surfactant-Based Colorimetric Detection of Plasmodium Lactate Dehydrogenase, a Biomarker for Malaria, Using the Specific DNA Aptamer. Plos One 2014, 9 (7), e100847.
Liu, H et al. Functional analysis of Orco and odorant receptors in odor recognition in Aedes albopictus. Parasites & Vectors (2016) 9:363.
Liu, J.; Lu, Y., Preparation of aptamer-linked gold nanoparticle purple aggregates for colorimetric sensing of analytes. Nature Protocols 2006, 1 (1), 246-252.
Long, T., Murdock, L. Stimulation of blowfly feeding behavior by octopaminergic drugs. P Natl Acad Sci USA 1983, 80 (13) 4159-4163.
Macdougall, G. J. Addis, N. Mackay, I. W. Dymock, A. G. G. Turpie, D. L. K. Ballingall,. W. J. Maclennan, B. Whiting, J. G. Macarthur. Treatment of Hypertension with Clonidine. British Medical_ Journal, 1970, 3, 440-442.
Ming, X., Mulvey, M., Mohanty, S., Patey, V. Safety and Efficacy of Clonidine and Clonidine Extended-Release in the Treatment of Children and Adolescents with Attention Deficit and Hyperactivity Disorders. Adolescent Health, Medicine and Therapeutics. 2011:2 105-112.
Moreira, JN., Gaspar, R. Antagonist G-Mediated Targeting and Cytotoxicity of Liposomal Doxorubicin in NCI-H82 Variant Small Cell Lung Cancer. Brazilian Journal of Medical and Biological Research. 2004. 37: 1185-1192.
Orlandi-Pradines et al., Antibody response against saliva antigens of Anopheles gambiae and Aedes aegypti in travellers in tropical Africa, Microbes and Infection 9 (2007) 1454-1462.
Peng et al., Production and characterization of monoclonal antibodies to two new mosquito *Aedes aegypti* salivary proteins. Insect Biochemistry and Molecular Biology 29 (1999) 909-914.
Radford, J., Davies, S., Dow, J. Systematic G-protein-coupled Receptor Analysis in *Drosophila melanogaster* Identifies a Leucokinin Receptor with Novel Roles. The Journal of Biological Chemistry. 2002, 38810-38817. DOI 10.1074/jbc.M203694200.
Remoue, F.; Cisse, B.; Ba, F. T.; Sokhna, C.; Herve, J. P.; Boulanger, D.; Simondon, F., Evaluation of the antibody response to Anopheles salivary antigens as a potential marker of risk of malaria. Transactions of the Royal Society of Tropical Medicine and Hygiene 2006, 100 (4), 363-370.
Siju KP, Reifenrath A, Scheiblich H, Neupert S, Predel R, Bill S. Hansson, Joachim Schachtner,Rickard Ignel. Neuropeptides in the Antennal Lobe of the Yellow Fever Mosquito, *Aedes aegypti*. The Journal of Comparative Neurology 2014 522:592-608.
Siju, KP., Hansson, B., Ignell, R. Immunocytochemical Localization of Serotonin in the Central and Peripheral Chemosensory System of Mosquitoes. Arthropod Structure & Development, 2008, 248-259.
Song K-M, Lee S, Ban C. Aptamers and Their Biological Applications. Sensors. 2012;12(1):612-631.
Sparks JT, Dickens JC, Mini Review: Gustatory Reception of Chemicals Affecting Host Feeding in Aedine Mosquitoes. Pesticide Biochemistry and Physiology (2017), 15-20. http://dx.doi.org/10.1016/j.pestbp.2016.12.009.
Storhoff JJ, Elghanian R, Mucic RC, Mirkin CA, Letsinger RL. One-pot colorimetric differentiation of polynucleotides with single base imperfections using gold nanoparticle probes. Journal of the American Chemical Society. 1998. 120;9 p. 1959-1964.
Takken W, Knols BG, Odor-Mediated Behavior of Afrotropical Malaria Mosquitoes, (1999) Annu. Rev. Entomol. 44:131-57.
Tuerk, C. & Gold, L. Systematic evolution of ligands by exponential enrichment: RNA ligands to bacteriophage T4 DNA polymerase. Science 249, 505-510 (1990).
Vleugels, R., Verlinden, H., Vanden Broeck, J. Serotonin, Serotonin Receptors and Their Actions in Insects. Neurotransmitter. 2015. 2: e314. doi: 10.14800/nt.314.
Weaver, S. C.; Scott, T. W.; Lorenz, L. H., Patterns of Eastern Equine Encephalomyelitis Virus-Infection In Culiseta-Melanura (Diptera, Culicidae). Journal of Medical Entomology 1990, 27 (5), 878-891.
Werner-Reiss, U. et al. Sensitivity of the Mosquito Aedes Aegypti (Culicidae) Labral Apical Chemoreceptors to Phagostimulants. Journal of Insect Physiology 45 (1999) 629-636.
Woll, P., Rozengurt, E. A Neuropeptide Antagonist That Inhibits the Growth of Small Cell Lung Cancer in Vitro. Cancer Research. 1990. 50, 3968-3973.
Zhou, C., Rao, Y., Rao, Y. A Subset of Octopaminergic Neurons are Important for *Drosophila* Aggression. Nature Neuroscience, 2008, 9 pages. doi:10.1038/nn.2164.

* cited by examiner

A

Clonidine

B

Pargyline

C

TCB-2

D

Polygodial

E

Arg-D-Trp-N(Me)Phe-D-Trp-Leu-Met-$NH_2$

Antagonist G

COMPOSITIONS FOR NEUROMODULATION OF MOSQUITO FEEDING BEHAVIOR AND USES THEREOF

CROSS REFERENCE TO RELATED APPLICATIONS

This application claims the benefit of U.S. Provisional Patent Application Ser. No. 62/556,643 filed Sep. 11, 2017, and U.S. Provisional Patent Application Ser. No. 62/585,707 filed Nov. 14, 2017, the disclosures of which are expressly incorporated herein by reference.

FIELD

The present disclosure relates to compositions and methods for enhancing mosquito feeding.

BACKGROUND

Mosquitoes continue to be the largest threat to global health. Their ability to vector deadly diseases such as Zika, dengue and chikungunya make mosquito control an indispensable tool for protecting public health. An estimated 390 million cases of dengue infections in over 120 countries are thought to occur every year. Since 2015, there have been over 5,000 reported cases of Zika in the United States and over 38,000 cases reported in US territories. The link between Zika and conditions such as microcephaly and Guillen-Barre have further heightened the need to control vector populations in the US and around the world.

Mosquitoes and other hematophagous insects rely on a myriad of sensory cues such as heat, carbon dioxide, salts and sugars to locate a host and to determine whether or not to feed. Reception of these cues is achieved by receptors for odorants, sugars, nucleotides, neuropeptides and heat. Each of these senses can either tune a mosquito to a host or away from a noxious stimulus. This host-seeking behavior is imperative to mosquito biology as blood feeding is required for egg development. Whether a mosquito imbibes a sugar meal or a blood meal, sensory information is provided to the mosquito via molecules and factors within the solution. In blood, these include soluble molecules such as adenosine triphosphate (ATP) or volatiles such as 4-ethylphenol (4EP) or cyclohexanol. These factors aid in the location of host vasculature, inform the mosquito to engorge and direct the meal to the midgut instead of the crop.

Passive devices are one method used to detect mosquitoes and/or pathogens that infect the mosquitoes. These unpowered devices can use colorimetric detection using DNA aptamer-gold nanoparticle conjugates (Au-aptamers). However, mosquito feeding is variable, with a number of mosquitoes showing insufficient feeding to be included in the colorimetric detection analysis. What is needed are novel compositions and methods for enhancing mosquito feeding behavior, which could aid in visualization of colorimetric detection of mosquitoes and/or detection of pathogens infecting mosquitoes.

The compositions and methods disclosed herein address these and other needs.

SUMMARY

Disclosed herein are compositions and methods for the neuromodulation and enhancement of the feeding behavior of mosquitoes. Further disclosed are devices and methods for increasing the level of engorgement of the mosquito on a diagnostic solution. The inventors have identified mosquito neuromodulation agents that can increase mosquito engorgement in order to aid in visual detection of mosquitoes and/or detection of disease states via colorimetric detection of proteins with aptamer gold-nanoparticle conjugates.

In some aspects, disclosed herein is a composition comprising: (a) a mosquito food source; and (b) a mosquito neuromodulation agent; wherein the mosquito neuromodulation agent increases the feeding behavior of the mosquito.

In some embodiments, the mosquito food source is sucrose. In some embodiments, the sucrose is present at about 10% sucrose. In some embodiments, the composition further comprises 15 mM NaCl, 1 mM $NaHCO_3$, 1 μM $MgCl_2$, 5 μM β,γ-methyleneadenosine 5'-triphosphate disodium salt (β,γ-met ATP), or a combination thereof.

In some embodiments, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

In some embodiments, the mosquito neuromodulation agent is selected from clonidine, pargyline, TCB-2, polygodial, antagonist G, or a combination thereof.

In some embodiments, the mosquito neuromodulation agent comprises clonidine. In some embodiments, the mosquito neuromodulation agent comprises pargyline. In some embodiments, the mosquito neuromodulation agent comprises TCB-2. In some embodiments, the mosquito neuromodulation agent comprises polygodial. In some embodiments, the mosquito neuromodulation agent comprises antagonist G.

In another aspect, disclosed herein is a method for enhancing mosquito feeding, comprising:

(a) providing a payload reservoir containing a composition, wherein the composition comprises:

a mosquito food source; and a mosquito neuromodulation agent; and (b) allowing mosquitoes to alight on or feed on the payload reservoir;

wherein the mosquito neuromodulation agent enhances mosquito feeding in comparison to a control composition without the mosquito neuromodulation agent.

In some embodiments, the mosquito food source is sucrose. In some embodiments, the sucrose is present at about 10% sucrose. In some embodiments, the composition further comprises 15 mM NaCl, 1 mM $NaHCO_3$, 1 μM $MgCl_2$, 5 μM β,γ-methyleneadenosine 5'-triphosphate disodium salt (β,γ-met ATP), or a combination thereof.

In some embodiments, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

In some embodiments, the mosquito neuromodulation agent is selected from clonidine, pargyline, TCB-2, polygodial, antagonist G, or a combination thereof.

In some embodiments, the mosquito neuromodulation agent comprises clonidine. In some embodiments, the mosquito neuromodulation agent comprises pargyline. In some embodiments, the mosquito neuromodulation agent comprises TCB-2. In some embodiments, the mosquito neuromodulation agent comprises polygodial. In some embodiments, the mosquito neuromodulation agent comprises antagonist G.

In some embodiments, the composition further comprises a detector conjugate, wherein the detector conjugate comprises a gold nanoparticle conjugated to a specific detector molecule. In some embodiments, the mosquito neuromodulation agent enhances mosquito feeding by at least 10%. In some embodiments, the mosquitoes are *Aedes aegypti.*

BRIEF DESCRIPTION OF THE DRAWINGS

The accompanying figures, which are incorporated in and constitute a part of this specification, illustrate several aspects described below.

DETAILED DESCRIPTION

Figure 1:
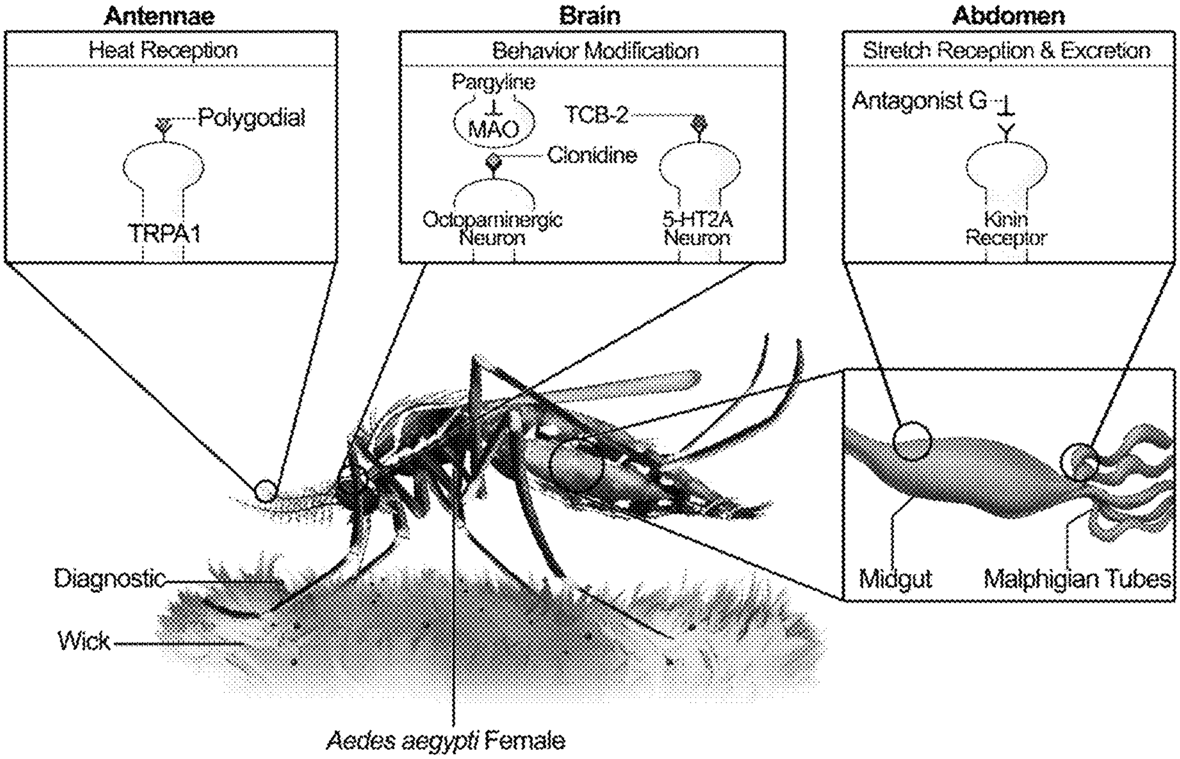
FIG. 1 shows a schematic for the neuromodulation of mosquito feeding behavior. Mosquitoes feeding on diagnostic solution laced with various drugs (neuromodulation agents) show variable engorgement rates based on drug combinations and dosing.

Disclosed herein are compositions and methods for the neuromodulation and enhancement of the feeding behavior of mosquitoes. Further disclosed are devices and methods for increasing the level of engorgement of the mosquito on a diagnostic solution. The inventors have identified mosquito neuromodulation agents that can increase mosquito engorgement in order to aid in visual detection of mosquitoes and/or detection of disease states via colorimetric detection of proteins with aptamer gold-nanoparticle conjugates.

Reference will now be made in detail to the embodiments of the invention, examples of which are illustrated in the drawings and the examples. This invention may, however, be embodied in many different forms and should not be construed as limited to the embodiments set forth herein.

Definitions

In the description that follows, a number of terms are used. In order to provide a clear and consistent understanding of the specification and claims, including the scope to be given such terms, certain definitions follow.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

The present invention is more particularly described in the following embodiments and examples that are intended to be illustrative only because numerous modifications and variations therein will be apparent to those skilled in the art. As used in the specification and in the claims, the singular for "a," "an" and "the" include plural referents unless the context clearly dictates otherwise.

Any reference in this specification to "one embodiment," "an embodiment," "example embodiment," "further embodiment," "alternative embodiment," "some embodiments," etc., is for literary convenience. The implication is that any particular feature, structure, or characteristic described in connection with such an embodiment is included in at least one embodiment of the invention. The appearance of such phrases in various places in the specification does not necessarily refer to the same embodiment. Further, when a particular feature, structure, or characteristic is described in connection with any embodiment, it is within the purview of one skilled in the art to affect such feature, structure, or characteristic in connection with other ones of the embodiments.

The term "insect" as used herein, describes any arthropod species desired to be attracted, monitored, surveilled, quantitated or discovered, in particular, species known as disease-vectoring species. This can include, but is not limited to, mosquitoes, flies, sand flies, tsetse flies, black flies, ticks, lice, midges, fleas, mites, wasps, bees, cockroaches, ants, bedbugs, triatomine bugs, etc. However, the compositions, devices, and methods disclosed herein can also be utilized with other arthropod or even non-arthropod species. Thus, it should be understood that the term "insect" or "mosquito" is used for literary convenience and is not meant to imply any limitation regarding the use of the embodiments of the subject invention.

The term "disease vector" refers to any agent, such as an insect, that carries and transmits an infectious pathogen into another living organism. Insects are specifically included in this definition. The term "disease" refers to any infectious pathogen, including but not limited to, a virus, bacterium or parasite.

The term "detector molecule" or "sensor molecule" refers to any aptamer or antibody (polyclonal or monoclonal) or binding fragment thereof that specifically binds to a compound to be detected. The term includes aptamers, antibodies, and binding fragments thereof that are conjugated to a label of any kind which allows the aptamer, antibody or binding fragment thereof to be visualized or otherwise detected. The term therefore specifically includes gold conjugates of the aptamer, monoclonal antibody or binding fragment thereof. The term "detector conjugate" refers to a detector molecule conjugated to one or more gold nanoparticles.

The term "delivery device," "sensor device" or "device" refers to a mechanism for providing to insects to be detected an attractant or feeding solution upon which the insect can alight and feed, simultaneously depositing on said device identifiable proteins. The term also includes any such mechanism that includes a detector molecule. Appropriate devices as meant by the term are described in United States Patent Publication No. 2015-0020439, the disclosures of which are hereby incorporated by reference; these devices are included in the meaning of the terms "delivery device," "sensor device" or "device."

The terms "payload," "payload solution," "payload contents" and "feeding solution," refer to a liquid composition to be made available to insects to be detected. The payload includes control solutions which contain no active ingredient, simple feeding solutions which are designed solely to provide one or more nutrients to the insects, solutions containing mosquito neuromodulation agents, solutions containing detector molecules such as the gold conjugates described herein and solutions containing any additional components such as insect attractants, insect repellants, insecticides, pheromones, preservatives, buffers, surfactants, or any component discernable by a skilled artisan. Any liquid or solution contained or to be contained within the internal payload reservoir is included within the definition of these terms.

The term "internal payload reservoir" or "payload reservoir" refers to any container for enclosing a liquid payload, payload solution, feeding solution, solid payload, or gaseous payload for release or to be made available for feeding or attraction of insects for detection.

The term "insect" in the context of this invention, refers to any of the arthropods that have a chitinous exoskeleton, a three-part body, and three pairs of jointed legs, i.e., any of the members of the Class Insecta. Mosquitoes are specifically included in this definition, including, but not limited to: *Aedes* (*Ae.*) *aegypti, Ae. vexans, Ae. albopictus, Ae. togoi, Ae. triseriatus, Aedes arabiensis, Culex* (*Cx.*) *quinquefasciatus, Cx. pipiens, Cx. tarsalis, Anopheles* (*An.*) *sinensis*, and *Culiseta* (*Cs.*) *inornata.*

The term "mosquito neuromodulation agent" refers to a compound that modulates the feeding behavior of a mosquito. As used herein, the mosquito neuromodulation agent increases the feeding behavior of the mosquito. The mosquito neuromodulation agent may increase the percentage of mosquitoes feeding, increase the amount of feeding solution taken up by the insect, or increase the percentage of mosquitoes feeding to higher amounts (for example, to "good" or "great" levels as discussed in the disclosure below).

Compositions and Methods

Disclosed herein are compositions and methods for the neuromodulation and enhancement of the feeding behavior of mosquitoes. Further disclosed are devices and methods for increasing the level of engorgement of the mosquito on a diagnostic solution by the mosquito (for example, the vector species *Aedes aegypti*). The inventors have identified mosquito neuromodulation agents that can increase mosquito engorgement in order to aid in visual detection of mosquitoes and/or disease states via colorimetric detection of mosquito proteins with aptamer gold-nanoparticle conjugates.

In some aspects, disclosed herein is a composition comprising: (a) a mosquito food source; and (b) a mosquito neuromodulation agent; wherein the mosquito neuromodulation agent increases the feeding behavior of the mosquito.

In some embodiments, the mosquito food source is sucrose. In some embodiments, the sucrose is present at about 10% sucrose. In some embodiments, the sucrose is present at about 1%, about 5%, about 10%, about 15%, about 20%, or about 25% sucrose. In some embodiments, the composition further comprises 15 mM NaCl, 1 mM $NaHCO_3$, 1 μM $MgCl_2$, 5 μM β,γ-methyleneadenosine 5'-triphosphate disodium salt (β,γ-met ATP), or a combination thereof. In some embodiments, the composition further comprises 15 mM NaCl. In some embodiments, the composition further comprises about 1 mM, about 5 mM, about 10 mM, about 15 mM, about 25 mM, about 50 mM, about 100 mM, about 150 mM, about 250 mM, or about 500 mM NaCl. In some embodiments, the composition further comprises 1 mM $NaHCO_3$. In some embodiments, the composition further comprises about 0.1 mM, about 0.5 mM, about 0.75 mM, about 1 mM, about 2.5 mM, about 5 mM, about 10 mM, about 15 mM, about 25 mM, or about 50 mM $NaHCO_3$. In some embodiments, the composition further comprises 1 μM $MgCl_2$. In some embodiments, the composition further comprises about 0.1 μM, about 0.5 μM, about 0.75 μM, about 1 μM, about 2.5 μM, about 5 μM, about 10 μM, about 15 μM, about 25 μM, or about 50 μM $MgCl_2$. In some embodiments, the composition further comprises 5 μM β,γ-methyleneadenosine 5'-triphosphate disodium salt (β,γ-met ATP). In some embodiments, the composition further comprises about 0.1 μM, about 0.5 μM, about 0.75 μM, about 1 μM, about 2.5 μM, about 5 μM, about 10 μM, about 15 μM, about 25 μM, about 50 μM, or about 100 μM β,γ-methyleneadenosine 5'-triphosphate disodium salt (β,γ-met ATP). In some embodiments, the composition further comprises about 15 mM NaCl. In some embodiments, the composition further comprises about 1 mM $NaHCO_3$. In some embodiments, the composition further comprises about 1 μM $MgCl_2$. In some embodiments, the composition further comprises about 5 μM β,γ-methyleneadenosine 5'-triphosphate disodium salt (β,γ-met ATP).

Sugar feeding solution #11 as described herein comprises, 10% sucrose, 15 mM NaCl, 1 mM $NaHCO_3$, 1 μM $MgCl_2$, and 5 μM β,γ-methyleneadenosine 5'-triphosphate disodium salt (β,γ-met ATP). Although sugar feeding solution #11 was found in the examples below to provide superior results, any mosquito feeding source can be used, and any of the component amounts in the mosquito feeding solution can be varied according as needed for different insects and different environments.

In some embodiments, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

In some embodiments, the mosquito neuromodulation agent is selected from clonidine, pargyline, TCB-2, polygodial, antagonist G, or a combination thereof.

In some embodiments, the mosquito neuromodulation agent comprises clonidine. In some embodiments, the mosquito neuromodulation agent comprises pargyline. In some embodiments, the mosquito neuromodulation agent comprises TCB-2. In some embodiments, the mosquito neuromodulation agent comprises polygodial. In some embodiments, the mosquito neuromodulation agent comprises antagonist G.

In some embodiments, the mosquito neuromodulation agent comprises the combination of clonidine, pargyline and polygodial. In some embodiments, the mosquito neuromodulation agent comprises the combination of clonidine, TCB-2, pargyline and polygodial. In some embodiments, the mosquito neuromodulation agent comprises the combination of 50 μM clonidine, 10 μM TCB-2, 10 μM pargyline, and 1 μM polygodial.

In some embodiments, the mosquito neuromodulation agent comprises the combination of clonidine, TCB-2, and pargyline. In some embodiments, the mosquito neuromodulation agent comprises the combination of 50 μM clonidine, 50 μM TCB-2, and 50 μM pargyline.

In some embodiments, the mosquito neuromodulation agent comprises the combination of clonidine, polygodial, and antagonist G. In some embodiments, the mosquito neuromodulation agent comprises the combination of 50 μM clonidine, 10 μM polygodial and 1 μM antagonist G. In some embodiments, the mosquito neuromodulation agent comprises the combination of clonidine and polygodial. In some embodiments, the mosquito neuromodulation agent comprises the combination of 40 μM clonidine and 1 μM polygodial.

In some embodiments, the mosquito neuromodulation agent comprises about 1 μM, about 5 μM, about 10 μM, about 20 μM, about 30 μM, about 40 μM, about 50 μM, about 60 μM, about 70 μM, about 80 μM, about 90 μM, about 100 μM, about 250 μM, or about 500 μM clonidine. In some embodiments, the mosquito neuromodulation agent comprises about 1 μM, about 5 μM, about 10 μM, about 20 μM, about 30 μM, about 40 μM, about 50 μM, about 60 μM, about 70 μM, about 80 μM, about 90 μM, about 100 μM, about 250 μM, or about 500 μM TCB-2. In some embodiments, the mosquito neuromodulation agent comprises about 1 μM, about 5 μM, about 10 μM, about 20 μM, about 30 μM, about 40 μM, about 50 μM, about 60 μM, about 70 μM, about 80 μM, about 90 μM, about 100 μM, about 250 μM, or about 500 μM pargyline. In some embodiments, the mosquito neuromodulation agent comprises about 0.05 μM, about 0.1 μM, about 0.5 μM, about 1 μM, about 5 μM, about 10 μM, about 50 μM, or about 100 μM polygodial. In some embodiments, the mosquito neuromodulation agent comprises about 0.05 μM, about 0.1 μM, about 0.5 μM, about 1 μM, about 5 μM, about 10 μM, about 50 μM, or about 100 μM antagonist G.

In another aspect, disclosed herein is a method for enhancing mosquito feeding, comprising:

(a) providing a payload reservoir containing a composition, wherein the composition comprises:

a mosquito food source; and a mosquito neuromodulation agent; and (b) allowing mosquitoes to alight on or feed on the payload reservoir;

wherein the mosquito neuromodulation agent enhances mosquito feeding in comparison to a control composition without the mosquito neuromodulation agent.

In another aspect, disclosed herein is a method for enhancing mosquito feeding, comprising:

(a) providing a payload reservoir containing a composition, wherein the composition comprises:

a mosquito food source; and a mosquito neuromodulation agent;

(b) allowing mosquitoes to alight on or feed on the payload reservoir; and (c) visualizing or quantitating the mosquitoes feeding;

wherein the mosquito neuromodulation agent enhances mosquito feeding in comparison to a control composition without the mosquito neuromodulation agent.

In some embodiments, the mosquito food source is sucrose. In some embodiments, the sucrose is present at about 10% sucrose. In some embodiments, the composition further comprises 15 mM NaCl, 1 mM $NaHCO_3$, 1 μM $MgCl_2$, 5 μM β,γ-methyleneadenosine 5'-triphosphate disodium salt (β,γ-met ATP), or a combination thereof. In some embodiments, the composition further comprises 15 mM NaCl. In some embodiments, the composition further comprises 1 mM $NaHCO_3$. In some embodiments, the composition further comprises 1 μM $MgCl_2$. In some embodiments, the composition further comprises 5 μM β,γ-methyleneadenosine 5'-triphosphate disodium salt (β,γ-met ATP). In some embodiments, the composition further comprises about 15 mM NaCl. In some embodiments, the composition further comprises about 1 mM $NaHCO_3$. In some embodiments, the composition further comprises about 1 μM $MgCl_2$. In some embodiments, the composition further comprises about 5 μM β,γ-methyleneadenosine 5'-triphosphate disodium salt β,γ-met ATP). Sugar feeding solution #11 as described herein comprises, 10% sucrose, 15 mM NaCl, 1 mM $NaHCO_3$, 1 μM $MgCl_2$, and 5 μM β,γ-methyleneadenosine 5'-triphosphate disodium salt (β,γ-met ATP). Although sugar feeding solution #11 was found in the examples below to provide superior results, any mosquito feeding source can be used, and any of the component amounts in the mosquito feeding solution can be varied according as needed for different insects and different environments.

In some embodiments, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

In some embodiments, the mosquito neuromodulation agent is selected from clonidine, pargyline, TCB-2, polygodial, antagonist G, or a combination thereof. In some embodiments, the mosquito neuromodulation agent is selected from 50 μM clonidine, 10 μM TCB-2, 10 μM pargyline, 1 μM polygodial, 1 μM antagonist G, or a combination thereof.

Figure 3:
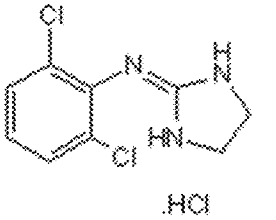
FIG. 3 shows the chemical structures for (A) clonidine, (B) pargyline, (C) TCB-2, (D) polygodial and (E) Antagonist G.
Figure 3:
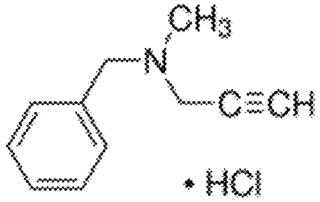
Figure 3:
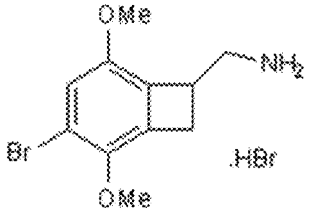
Figure 3:
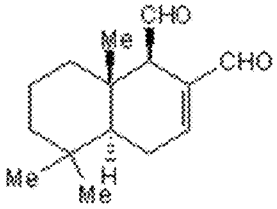

In some embodiments, the mosquito neuromodulation agent comprises clonidine. In some embodiments, the mosquito neuromodulation agent comprises pargyline. In some embodiments, the mosquito neuromodulation agent comprises TCB-2. In some embodiments, the mosquito neuromodulation agent comprises polygodial. In some embodiments, the mosquito neuromodulation agent comprises antagonist G. The chemical structures of clonidine, pargyline, TCB-2, polygodial, and antagonist G are shown in FIG. 3.

In some embodiments, the mosquito neuromodulation agent comprises the combination of clonidine, pargyline and polygodial. In some embodiments, the mosquito neuromodulation agent comprises the combination of clonidine, TCB-2, pargyline and polygodial. In some embodiments, the composition further comprises a detector conjugate, wherein the detector conjugate comprises a gold nanoparticle conjugated to a specific detector molecule.

In some embodiments, the mosquito neuromodulation agent enhances mosquito feeding by at least 10% (for example, at least 10%, at least 20%, at least 30%, at least 40%, at least 50%, at least 60%, at least 70%, at least 80%, at least 90%, at least 100%, etc.). In some embodiments, the mosquitoes are *Aedes aegypti.*

In some embodiments, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

Table 3 lists non-limiting examples of octopaminergic agonists, MAO-B inhibitors, 5-HT2A agonists, TRPA1 agonists, and broad-spectrum neuropeptide receptor agonists.

Octopamine, as well as its counterpart tyramine, function through G-protein coupled receptors in invertebrates and serve as the analogues of adrenergic signaling in vertebrates. Octopamine receptors are present throughout the bodies of flies and have control over feeding, aggression, memory and muscle contractions. To increase feeding, clonidine or pargyline can be administered. Clonidine is an agonist of octopamine receptors which has previously been shown to decrease oviposition and larval hatch rate in *Anopheles gambiae*. Other octopamine receptor agonists include arylethanolamines (AEAs) and 2-(arylimino) thiazolidines (AITs) which have been studied in the cockroach nervous system.

Pargyline is a monoamine oxidase (MAO-B) inhibitor that prolongs octopamine in the synaptic cleft by inhibiting its breakdown. Selegiline and rasagiline are other MAO-B inhibitors that are FDA approved and used commercially.

Serotonin, also called 5-Hydroxytryptamine (5-HT), signaling has also been shown to affect feeding, amongst other behaviors, in mosquitoes. 5-HT acts through its receptors which have been categorized into seven families denoted as 5-HT1-7. These receptors are rhodopsin-like G-protein coupled receptors except for 5-HT3 which acts as a ligand gated ion channel. 5-HT receptors can be further divided based upon their downstream signaling pathways and whether or not they activate or inhibit proteins such as Adenylate Cyclase or Phospholipase C. Of note, 5-HT2A has been shown to affect engorgement rates in *drosophila* larvae, with knock outs of 5-HT2A showing decreased engorgement rates. The 5-HT2A receptor was agonized using the 5-HT2A specific agonist TCB-2. Other agonists of 5-HT2A include mexamine and 1-isopropyl-6-fluoro-psilocin (O-4310). Contradictory to insects, agonizing this receptor has shown to decrease feeding behavior in food-deprived mice. This could prove to be a possible divergence in the signaling pathways of serotonin in mammals and insects.

Leucokinin, the invertebrate analogue of vertebrate tachykinin, is a neuropeptide that possesses a broad range of effects in the gut, malpighian tubes and the periphery. Acting upon stellate cells in the Malpighian tubes, leucokinin has a diuretic effect by increasing chloride secretion. In the midgut, leucokinin facilitates feedback signals caused by gut distention following meal intake. This is evidenced by knock outs of either the peptide or its receptor causing increased engorgement in *Drosophila*. More recently, leucokinin has been shown to have effects on the periphery, as well. Agonizing leucokinin receptors on the tarsi or labella of *Ae. aegypti* elicited a strong aversive effect and decreased sugar sensing neurons ability to function. To target these peripheral sensory neurons as well as the Malpighian tubes, a broad-spectrum neuropeptide receptor (kinin) antagonist, Antagonist G, was added to the diagnostic solution to increase the feeding behavior and decrease fluid secretion in the mosquitoes. Additional examples of broad-spectrum neuropeptide receptor antagonists include, for example, kinin and bradykinin antagonists (such as flavonoids apiin and hesperitin) or biostable analogs are used that are specific to particular kinin receptors which are matched with the corresponding receptors in mosquitoes.

In addition to biogenic amines and neuropeptides, thermoreception plays an important role in host seeking and engorgement rates in mosquitoes. Mosquitoes have previously been shown to imbibe on average 0.7 μl of room temperature blood while 3.4 μl of blood warmed to 37° C. will be imbibed. Heat reception also plays an important role in host seeking behavior and aversion from hot surfaces.

The heat sensing protein TRPA1 is involved in thermotaxis towards a host. Knocking out this receptor also increases occupancy on surfaces with temperatures above 55° C. which wild type animals perceived as noxious. This suggests that TRPA1 acts not only to tune mosquitoes to warm-bodies hosts but also will steer mosquitoes away from harmful temperatures above 55° C. To agonize TRPA1 receptors, the drug polygodial, the active constituent of several types of peppers, was used. Polygodial has previously been shown to have repellant ability in mosquitoes and act as a larvacide. Noticing a possible biphasic effect of polygodial on mosquitoes, dosing was examined to determine at what level polygodial is attractive rather than aversive to mosquitoes. Other TRPA1 agonists include allyl isothiocyanate and cinnamaldehyde.

The compositions disclosed herein can be used in any passive device known in the art for detecting mosquitoes or detecting pathogens within the mosquitoes. For example, the devices can be those found in WO/2017/027677, which is herein incorporated by reference.

In some aspects, provided herein is a kit comprising: a mosquito food source; and a mosquito neuromodulation agent. In some embodiments, the kit further comprises instructions for refilling a device with the kit components.

In some embodiments, the kit comprises sucrose and a mosquito neuromodulation agent. In some embodiments, the kit comprises sucrose and clonidine. In some embodiments, the kit comprises sucrose and pargyline In some embodiments, the kit comprises sucrose and TCB-2. In some embodiments, the kit comprises sucrose and polygodial. In some embodiments, the kit comprises sucrose and antagonist G.

In some aspects, the mosquito neuromodulation agent is comprised within a sensor device that further contains detector conjugates that can bind saliva proteins, or pathogen proteins found in the saliva, expectorated during mosquito sugar feeding. For example, the detector conjugates can be species-specific. In other aspects, the detector conjugates are pathogen-specific. In these embodiments, saliva expectorated by the species of mosquito on the device can result in agglomeration of the detector conjugates and development of a color change, such as a colored spot on the device.

For example, disclosed herein is a device comprising:

(a) a payload reservoir comprising a mosquito food source and a mosquito neuromodulation agent; and (b) a detector conjugate comprising a gold nanoparticle conjugated to a specific detector molecule that binds specifically to a protein present in the saliva of a specific mosquito to be detected;

wherein the mosquito neuromodulation agent increases the feeding behavior of the mosquito.

Also disclosed herein is a device comprising:

(a) a payload reservoir comprising a mosquito food source and a mosquito neuromodulation agent; and (b) a detector conjugate comprising a gold nanoparticle conjugated to a specific detector molecule that binds specifically to a pathogen protein present in the saliva of a mosquito infected by a pathogen; wherein the mosquito neuromodulation agent increases the feeding behavior of the mosquito.

Also provided herein is a method for detecting specific mosquitoes which may be located in an area which method comprises:

(a) providing in said area a sensor device which comprises: a payload reservoir comprising a mosquito food source and a mosquito neuromodulation agent, wherein the mosquito neuromodulation agent increases the feeding behavior of the mosquito; and a detector conjugate comprising a gold nanoparticle conjugated to a specific detector molecule that binds specifically to a protein present in the saliva of said specific mosquito to be detected;

(b) allowing said specific mosquitoes to alight on or feed on said sensor device under conditions suitable to allow the binding of said protein to said detector conjugate to form an agglomerated detector conjugate; and (c) visualizing or quantitating the binding of said protein to said detector conjugate to form an agglomerated detector conjugate to determine the presence of the protein.

Also provided herein is a method for detecting a mosquito infected with a pathogen which may be located in an area, the method comprising:

(a) providing in said area a sensor device which comprises: a payload reservoir comprising a mosquito food source and a mosquito neuromodulation agent, wherein the mosquito neuromodulation agent increases the feeding behavior of the mosquito; and a detector conjugate comprising a gold nanoparticle conjugated to a specific detector molecule that binds specifically to a pathogen protein present in the saliva of a mosquito infected by a pathogen;

(b) allowing said specific mosquitoes to alight on or feed on said sensor device under conditions suitable to allow the binding of said pathogen protein to said detector conjugate to form an agglomerated detector conjugate; and (c) visualizing or quantitating the binding of said pathogen protein to said detector conjugate to form an agglomerated detector conjugate to determine the presence of the pathogen protein.

In some aspects, disclosed herein is a method for detecting specific mosquitoes which may be located in an area which method comprises (a) providing in said area a sensor device which comprises a releasing wick, a detector conjugate comprising a gold nanoparticle conjugated to a specific detector molecule that binds specifically to a protein present in the saliva of said specific mosquito to be detected, and a mosquito food source; (b) allowing said specific mosquitoes to alight on or feed on said sensor device such that said protein binds to said detector conjugate; (c) exposing said bound detector conjugate to a concentration of NaCl of about 1 mM to about 1000 mM NaCl or more specifically 1-100 mM NaCl to agglomerate said bound detector conjugate; and (d) visualizing or quantitating said agglomerated detector conjugate. In a specific embodiment, the agglomerated detector conjugate is visualized or quantified in a NaCl concentration of about 250 mM. The term "about" as used herein refers to the stated amount and ±10% of the stated amount.

In some aspects, the disclosed sensor device contains detector conjugates that can bind pathogen proteins in a mosquito food source. In these embodiments, digestion of the food source by the mosquito results in agglomeration of the detector conjugates and development of a color change in the mosquito. This food source preferably also contains a toxic substance that kills the mosquito for collection and evaluation. The mosquito can therefore be collected and evaluated for color changes.

For example, provided herein is a method for detecting specific mosquitoes which may be located in an area which method comprises:

(a) providing in said area a sensor device which comprises: a payload reservoir comprising a mosquito food source and a mosquito neuromodulation agent, wherein the mosquito neuromodulation agent increases the feeding behavior of the mosquito; a toxic substance (e.g., toxic sugar water substance); and a detector conjugate comprising a gold nanoparticle conjugated to a specific detector molecule that binds specifically to a protein present in the saliva of said specific mosquito to be detected;

(b) allowing said specific mosquitoes to alight on or feed on said sensor device such that said detector conjugate is ingested by the mosquito, wherein said protein binds to said detector conjugate to form an agglomerated detector conjugate before, during, or after ingestion; and (c) visualizing or quantitating said agglomerated detector conjugate in the mosquito.

Also provided herein is a method for detecting a mosquito infected with a pathogen which may be located in an area, the method comprising:

(a) providing in said area a sensor device which comprises: a payload reservoir comprising a mosquito food source and a mosquito neuromodulation agent, wherein the mosquito neuromodulation agent increases the feeding behavior of the mosquito; a toxic substance (e.g., toxic sugar water substance); and a detector conjugate comprising a gold nanoparticle conjugated to a specific detector molecule that binds specifically to a pathogen protein present in the saliva of a mosquito infected by a pathogen;

(b) allowing said specific mosquitoes to alight on or feed on said sensor device such that said detector conjugate is ingested by the mosquito, wherein said protein binds to said detector conjugate to form an agglomerated detector conjugate before, during, or after ingestion; and (c) visualizing or quantitating said agglomerated detector conjugate in the mosquito.

In some embodiments, the insects (for example, mosquitoes) to be detected are disease vectors carrying a virus, bacterium or parasite which causes disease in mammals, and the protein specific to said insects to be detected is a virus, bacterium or parasite protein. The animal can be a human, a livestock animal, or any mammal.

In some embodiments, the neuromodulation agents disclosed herein can be used to modulate the feeding behavior of insects (including mosquitoes). Examples of diseases to be detected include but are not limited to Dengue fever, Zika fever, chikungunya, Rift Valley fever, yellow fever, malaria, Japanese encephalitis, Saint Louis encephalitis, lymphatic filariasis, West Nile fever, leishmaniasis, sandfly fever, Lyme disease, plague, tularemia, Chagas disease, and onchocerciasis, or any insect-borne disease. Therefore, the proteins to be detected by the sensor devices and methods of the invention preferably include, but are not limited to *P. falciparum* histidine-rich protein 2 (PFHRP2) and lactate dehydrogenase (PFLDH), viral envelope (capsid) or spike proteins/antigens on all viruses, flagellar proteins of bacterial pathogens, salivary proteins listed in table 1 of Z. Peng et al./Insect Biochemistry and Molecular Biology 29 (1999) 909-914, table 1 of E. Orlandi-Pradines et al./Microbes and Infection 9 (2007) 1454-1462, *Anopheles gambiae* salivary protein gSG6. One exemplary protein specific to said insects is mosquito salivary gland allergen Aed a 2.

In some embodiments, the specific detector molecule is aptazyme, apta-beacon, antibody (polyclonal or monoclonal) or a binding fragment thereof. In a specific embodiment, the detector molecule is an aptamer.

Further disclosed herein are methods according to the invention wherein the insect is selected from the group consisting of mosquitoes (*Aedes* spp., *Anopheles* spp., *Culex* spp.), flies, sand flies, tsetse flies, black flies, ticks, lice, midges, fleas, ticks, mites, and triatomine bugs. In some embodiments, the insect is a mosquito, such as those selected from the group consisting of, for example, *Aedes* (*Ae.*) *aegypti*, *Ae. vexans*, *Ae. albopictus*, *Ae. togoi*, *Ae. triseriatus*, *Aedes arabiensis*, *Culex* (*Cx.*) *quinquefasciatus*, *Cx. pipiens*, *Cx. tarsalis*, *Anopheles* (*An.*) *sinensis*, *Anopheles gambiae*, and *Culiseta* (*Cs.*) *inornata*.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Neuromodulation of Mosquito Feeding Behavior

Identifying infection states of arbovirus vectoring mosquitoes via gold nanoparticle-aptamer (AuNP-apt) sensing molecules is an important method for disease detection. This innovative technology includes increasing the volume of AuNP-apt diagnostic solution imbibed by mosquitoes. A fully engorged mosquito allows for easier visual confirmation of a red-to-blue color shift which occurs when aptamers bind to arbovirus proteins inside a mosquito's abdomen. Therefore, in this example, neuromodulation of sensory and satiety pathways were examined for an increase the level of engorgement on the diagnostic solution by the vector species *Aedes aegypti* (See FIG. 1). Several drugs targeting biogenic amine, TRPA1 and neuropeptide signaling were examined for increasing engorgement to aid in visual detection of disease states via a visible color shift caused by an AuNP-apt diagnostic.

Mosquitoes continue to be the largest threat to global health. Their ability to vector deadly diseases such as Zika, dengue and chikungunya make mosquito control an indispensable tool for protecting public health. An estimated 390 million cases of dengue infections in over 120 countries are thought to occur every year. Since 2015, there have been over 5,000 reported cases of Zika in the United States and over 38,000 cases reported in US territories. The link between Zika and conditions such as microcephaly and Guillen-Barre have further heightened the need to control vector populations in the US and around the world. One method that the Willenberg Lab is currently developing relies on the use of gold nanoparticle-aptamer conjugates to induce a visible color change in the mosquito abdomen for rapid, colorimetric detection of arboviruses. One facet of this ongoing project is to increase the engorgement rate of the diagnostic solution so that it is easier to view inside the clear abdomen of the mosquito. In this example, the feeding behavior of mosquitoes was modulated by lacing a diagnostic feeding solution with different drug compounds and the increase in engorgement rate was examined.

Mosquitoes and other hematophagous insects rely on a myriad of sensory cues such as heat, carbon dioxide, salts and sugars to locate a host and to determine whether or not to feed. Reception of these cues is achieved by receptors for odorants, sugars, nucleotides, neuropeptides and heat. Each of these senses can either tune a mosquito to a host or away from a noxious stimulus. This host-seeking behavior is imperative to mosquito biology as blood feeding is required for egg development. Whether a mosquito imbibes a sugar meal or a blood meal, sensory information is provided to the mosquito via molecules and factors within the solution. In blood, these include soluble molecules such as adenosine triphosphate (ATP) or volatiles such as 4-ethylphenol (4EP) or cyclohexanol. These factors aid in the location of host vasculature, inform the mosquito to engorge and direct the meal to the midgut instead of the crop. Directing the diagnostic solution to the midgut, much the same as blood is directed, aids in detection of arboviruses as the midgut is the first place an infection takes hold in a mosquito. Thus, a sugar based feeding solution was developed (described in methods) which is directed to the crop by adding a non-hydrolyzable ATP analog (β,γ-methyleneadenosine 5'-triphosphate disodium salt (β,γ-met ATP)). Visualizing this diagnostic solution inside the mosquito by eye requires a sufficient amount to be imbibed such that the abdomen of the mosquito stretches to provide easier viewing of the midgut contents. The neuromodulation of these insects was investigated as a method to trick the mosquito into fully engorging on a solution they normally would not drink to such volumes. This allows a researcher in the field to view the diagnostic solution inside the stretched abdomen of an engorged mosquito.

Induction of hyperphagia in insects was first accomplished by transecting the ventral nerve of a mosquito at different ganglia with the second ganglia yielding the greatest engorgement. Chemically induced hyperphagia was later accomplished in in a blow fly using compounds that targeted the receptor for octopamine, the dipthera analog of epinephrine. Biogenic amines such as octopamine, tyramine, serotonin and dopamine have since been shown to have a wide range of effects on mosquitoes and other insects including effects on feeding behavior, host seeking behavior, memory and the overall sensitivity of the central and peripheral nervous system. In the present example, different drugs (mosquito feeding agents), different concentrations, and synergistic effects were examined for an increase in engorgement in mosquitoes.

This example analyzes the effect of mosquito neuromodulation agents on modulating feeding behavior of mosquitoes. Here, the mosquito neuromodulation agent is selected from an octopaminergic agonist, a MAO-B inhibitor, a 5-HT2A agonist, a TRPA1 agonist, a broad-spectrum neuropeptide receptor agonist, or a combination thereof.

Octopamine, as well as its counterpart tyramine, function through G-protein coupled receptors in invertebrates and serve as the analogues of adrenergic signaling in vertebrates. Octopamine receptors are present throughout the bodies of flies and have control over feeding, aggression, memory and muscle contractions. To increase feeding, clonidine or pargyline were administered. Clonidine is an agonist of octopamine receptors which has previously been shown to decrease oviposition and larval hatch rate in *Anopheles gambiae*, and pargyline is a monoamine oxidase inhibitor that prolongs octopamine in the synaptic cleft by inhibiting its breakdown.

Serotonin, also called 5-hydroxytryptamine (5-HT), signaling has also been shown to affect feeding, amongst other behaviors, in mosquitoes. 5-HT acts through its receptors which have been categorized into seven families denoted as 5-HT1-7. These receptors are rhodopsin-like G-protein coupled receptors except for 5-HT3 which acts as a ligand gated ion channel. 5-HT receptors can be further divided based upon their downstream signaling pathways and whether or not they activate or inhibit proteins such as Adenylate Cyclase or Phospholipase C. Of note, 5-HT2A has been shown to affect engorgement rates in *drosophila* larvae, with knock outs of 5-HT2A showing decreased engorgement rates. The 5-HT2A receptor was agonized with TCB-2, a potent selective 5-HT2A agonist. Contradictory to insects, agonizing this receptor has shown to decrease feeding behavior in food-deprived mice. This could prove to be a possible divergence in the signaling pathways of serotonin in mammals and insects.

Leucokinin, the invertebrate analogue of vertebrate tachykinin, is a neuropeptide that possesses a broad range of effects in the gut, the malpighian tubes and the periphery. Acting upon stellate cells in the Malpighian tubes, leucokinin acts as a diuretic by increasing chloride secretion. In the midgut, leucokinin facilitates feedback signals caused by gut distention following meal intake. This is evidenced by knock outs of either the peptide or its receptor causing increased engorgement in *Drosophila*. More recently, leucokinin has been shown to have effects on the periphery, as well. Agonizing leucokinin receptors on the tarsi or labella of *Ae. aegypti* elicited a strong aversive effect and decreased sugar sensing neurons ability to function. To target these peripheral sensory neurons as well as the Malpighian tubes, a broad-spectrum neuropeptide receptor (kinin) antagonist, Antagonist G, was added to the diagnostic solution to increase the feeding behavior and decrease fluid secretion in the mosquitoes.

In addition to biogenic amines and neuropeptides, thermoreception plays an important role in host seeking and engorgement rates in mosquitoes. Mosquitoes have previously been shown to imbibe on average 0.7 ul of room temperature blood while 3.4 ul of blood warmed to 37° C. will be imbibed. Heat reception also plays an important role in host seeking behavior and aversion from hot surfaces.

The heat sensing protein TRPA1 is involved in thermotaxis towards a host. Knocking out this receptor also increases occupancy on surfaces with temperatures above 55° C. which wild type animals perceived as noxious. This suggests that TRPA1 acts not only to tune mosquitoes to warm-bodies hosts but also will steer mosquitoes away from harmful temperatures above 55° C. To agonize TRPA1 receptors, the drug polygodial, the active constituent of several types of peppers, was used. Polygodial has previously been shown to have repellant ability in mosquitoes and act as a larvacide. Noticing a possible biphasic effect of polygodial on mosquitoes, dosing was examined to determine at what level polygodial is attractive rather than aversive to mosquitoes.

Results and Discussion

Mosquitoes have Variable Engorgement Rates on the Sugar-Based Feeding Solution:

A sugar-based feeding solution was chosen as a base buffer for the development of Apt-AuNPs (called herein solution #11). This solution comprised sucrose as a phagostimulant, magnesium to stabilize the diagnostic aptamers, and a suitable pH to encourage mosquitoes to imbibe it. This solution is comprised of 10% sucrose, 15 mM NaCl, 1 mM $NaHCO_3$, 1 μM $MgCl_2$ and 5 μM β,γ-methyleneadenosine 5'-triphosphate disodium salt (β,γ-met ATP). Though solution #11 led to the greatest proportion of mosquitoes feeding upon it, the degree of engorgement was not only variable but was very low in some cases. This engorgement rate variability meant that some of the mosquitoes, though perhaps imbibing a small amount of the diagnostic, would not be easily characterized as it was difficult to see any diagnostic in their abdomen.

Mosquitoes Engorge More Frequently on Sugar-Based Feeding Solutions Laced with Neuromodulation Agents Compared to Feeding Solution or Sucrose Alone Drugs affecting different sensory pathways were added to the sugar based feeding solution in order to increase mosquito engorgement rates (outlined in Table 3).

TABLE 3

Description of compounds used in this example

| Drug | Description |
|---|---|
| Clonidine | α2-adrenergic agonist/Octopaminergic agonist |
| Pargyline | Monoamine Oxidase Inhibitor (MAO-B inhibitor) |
| TCB-2 | High affinity 5-$HT_{2A}$ agonist (5-HT2A agonist) |
| Polygodial | Selective TRPA1 agonist |
| Antagonist G | Broad-spectrum neuropeptide receptor antagonist |

The number of experiments, the percentage of feeding mosquitos, and the percentage of good-great feeding mosquitos with 95% confidence intervals for each experimental group are displayed in Table 4.

TABLE 4

Drug concentrations of experimental groups.

| Group | Base | Clonidine | TCB-2 | Pargyline | Polygodial | Antagonist G |
|---|---|---|---|---|---|---|
| Control A | 10% Sucrose | | | | | |
| Control B | # 11 | | | | | |
| 1 | # 11 | 100 nM | | | | |
| 2 | # 11 | 50 uM | | | | |
| 3 | # 11 | 100 uM | | | | |
| 4 | # 11 | 500 uM | | | | |
| 5 | # 11 | | | | 1000 nM | |
| 6 | # 11 | | | | 1 uM | |
| 7 | # 11 | | | | 10 uM | |
| 8 | #11 | 40 uM | | | 1 uM | |
| 9 | #11 | 50 uM | 50 uM | | | |
| 10 | # 11 | 50 uM | | | 1 uM | |
| 11 | # 11 | 50 uM | | | 10 uM | |
| 12 | # 11 | | 50 uM | | 1 uM | |
| 13 | # 11 | | 50 uM | 50 uM | | |
| 14 | # 11 | | | 50 uM | 1 uM | |
| 15 | # 11 | | | 50 uM | 10 uM | |
| 16 | # 11 | 50 uM | 50 uM | 50 uM | | |
| 17 | # 11 | 50 uM | | | 1 uM | 1 uM |
| 18 | # 11 | 50 uM | | | 10 uM | 1 uM |
| 19 | # 11 | 50 uM | | 10 uM | 1 uM | |
| 20 | # 11 | 50 uM | | 50 uM | 1 uM | |
| 21 | # 11 | | 50 uM | 50 uM | | 1 uM |
| 22 | # 11 | 50 uM | 10 uM | 10 uM | 1 uM | |
| 23 | # 11 | 50 uM | 50 uM | 50 uM | 1 uM | |
| 24 | # 11 | 50 uM | 10 uM | 10 uM | 1 uM | 1 uM |

Figure 2:
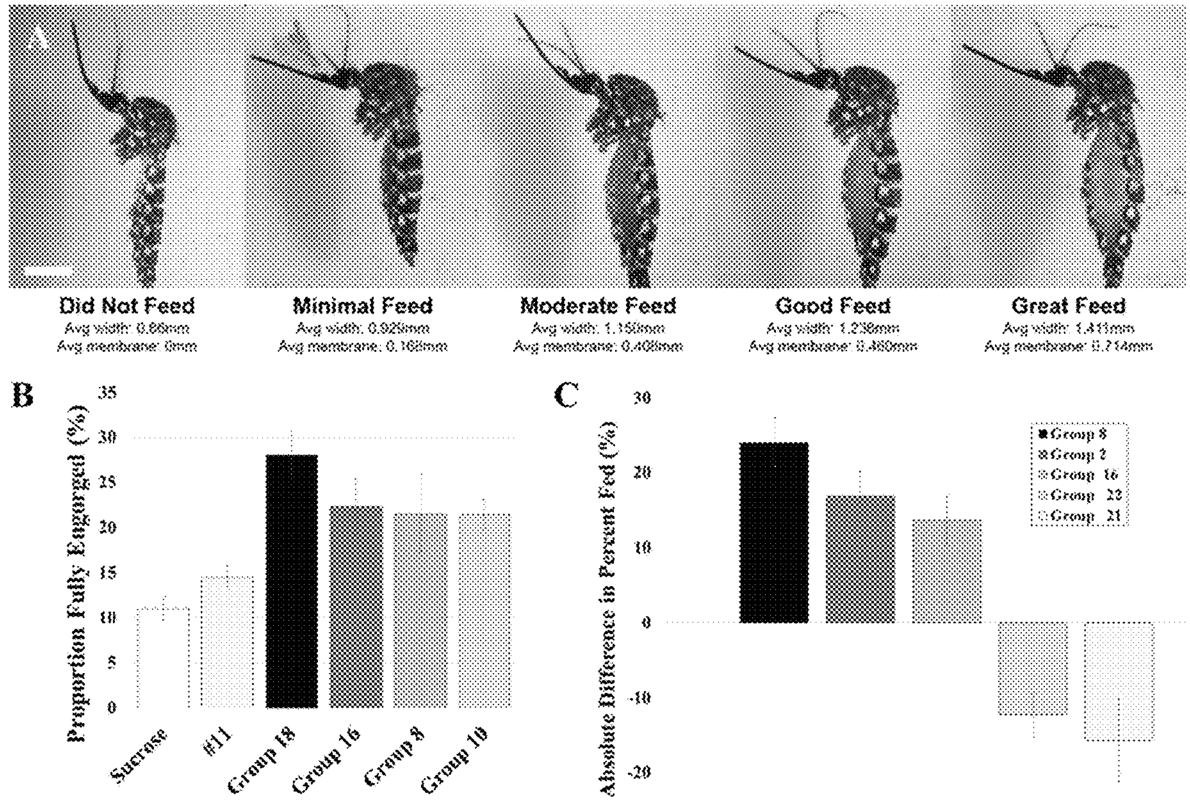
FIG. 2 shows the determination of mosquito engorgement using various neuromodulation agents. (A) Feeding experiment grading scheme. Engorgement defined as Good-Great range of gut distention. (B) Proportion of mosquitoes engorging on diagnostic solution with selected drug treatments. Group 18 (50 μM Clonidine, 10 μM Polygodial and 1 μM Antagonist G) yielded the greatest proportion of engorged mosquitoes. (C) Absolute difference of feeding rates on select treatment groups compared to control (solution #11). Group 8 (40 μM Clonidine and 1 μM Polygodial) yielded the greatest increase in the likelihood to feed at 24.1%. Scale bar=1 mm.

In Table 1 (and FIG. 2B), the results of the percentage of mosquitos that experienced good-great feeding (FIG. 2A) for each feeding group compared to control group B is depicted.

TABLE 1

Descriptive Feeding Statistics for Mosquito Experiments

| Experimental | Number of Experiments | Total Percent Fed | | Good-Great Percent Fed | |
|---|---|---|---|---|---|
| Group | n | % | 95% CI | % | 95% CI |
| Control A | 33 | 68.7 | 63.1-74.7 | 11.0 | 8.7-14.0 |
| Control B | 76 | 68.3 | 64.6-72.2 | 14.5 | 12.5-16.9 |
| Group 1 | 3 | 63.2 | 53.0-75.2 | 9.8 | 5.6-17.0 |
| Group 2 | 6 | 85.2 | 78.9-92.0 | 18.5 | 11.9-28.9 |
| Group 3 | 3 | 68.6 | 57.5-81.8 | 2.9 | 1.0-8.5 |
| Group 4 | 3 | 63.3 | 47.7-84.0 | 3.3 | 1.2-9.3 |
| Group 5 | 3 | 66.2 | 49.0-89.4 | 1.4 | 0.7-2.9 |
| Group 6 | 9 | 74.7 | 68.3-81.7 | 9.5 | 5.9-15.4 |
| Group 7 | 4 | 66.3 | 60.3-73.0 | 2.7 | 0.5-16.0 |
| Group 8 | 3 | 92.4 | 89.3-95.6 | 21.5 | 14.4-32.3 |
| Group 9 | 29 | 70.1 | 65.5-75.1 | 16.7 | 13.3-20.9 |
| Group 10 | 67 | 71.9 | 68.0-76.1 | 21.5 | 18.7-24.6 |

TABLE 1-continued

Descriptive Feeding Statistics for Mosquito Experiments

| Experimental | Number of Experiments | Total Percent Fed | | Good-Great Percent Fed | |
|---|---|---|---|---|---|
| Group | n | % | 95% CI | % | 95% CI |
| Group 11 | 13 | 67.6 | 59.8-76.4 | 17.6 | 12.4-25.1 |
| Group 12 | 5 | 60.2 | 47.9-75.7 | 6.2 | 1.6-23.7 |
| Group 13 | 8 | 65.8 | 58.8-73.5 | 13.8 | 10.8-17.7 |
| Group 14 | 9 | 65.8 | 56.9-76.0 | 16.8 | 12.6-22.2 |
| Group 15 | 3 | 73.6 | 68.4-79.2 | 18.8 | 16.0-22.0 |
| Group 16 | 4 | 81.9 | 71.7-93.5 | 22.3 | 17.4-28.7 |
| Group 17 | 15 | 71.3 | 66.5-76.6 | 20.2 | 15.3-26.7 |
| Group 18 | 9 | 73.0 | 62.0-86.0 | 28.0 | 23.1-34.1 |
| Group 19 | 28 | 60.4 | 52.3-69.7 | 15.0 | 10.6-21.3 |
| Group 20 | 5 | 67.3 | 57.0-79.4 | 17.9 | 9.5-33.7 |
| Group 21 | 3 | 52.6 | 47.5-58.3 | 18.1 | 16.2-20.1 |
| Group 22 | 27 | 56.1 | 48.1-65.4 | 16.5 | 12.5-21.7 |
| Group 23 | 7 | 60.3 | 43.4-84.0 | 10.6 | 5.7-19.6 |
| Group 24 | 4 | 57.6 | 46.6-71.1 | 10.5 | 8.2-13.4 |

Abbreviations:
CI, confidence interval.

Six groups experienced significantly better engorgement (good-great feeding) ranging from a high of 13.5% (Group 18) to 3.5% (Group 21) increased good-great feeding. Group 17 also experienced a 5.7% increased likelihood of good-great feeding although this result failed to reach statistical significance. Eight feeding groups also experienced a lower likelihood of good-great feeding compared to control group B. Some groups reached the threshold of borderline/marginally significant on one scale, but not the other. For example, on the absolute scale, mosquitos in Groups 6 and 12 were less likely to engage in good-great feeding but this result was not found on the relative scale. Likewise, Group 8 experienced a 48% increased likelihood of good-great feeding that was marginally significant, but this difference was not found on the absolute scale.

Groups that reached statistical significance or approached statistical significance in terms of better feeding and/or good-great feeding compared to Control Group B are denoted in Table 2.

TABLE 2

Absolute Differences and Relative Likelihoods of Feeding Compared to Control B

| Experimental | Absolute percent difference | | | Relative likelihood | | |
|---|---|---|---|---|---|---|
| Group | % | 95% CI | P | RR | 95% CI | P |
| Clon 40 uM, Poly 1 uM | 24.1 | 19.1-29.0 | <0.01 | 1.35 | 1.27-1.41 | <0.01 |
| Clon 50 uM, | 16.9 | 9.3-24.5 | <0.01 | 1.25 | 1.13-1.37 | <0.01 |
| Clon 50 uM TCB-2 50 uM, Parg 50 uM | 13.6 | 2.1-25.1 | 0.02 | 1.20 | 1.04-1.39 | 0.01 |
| Clon 50 uM TCB-2 10 uM, Parg 10 uM, Poly 1 uM | −12.2 | −21.6--2.8 | 0.01 | 0.82 | 0.70-0.97 | 0.02 |
| TCB-2 50 uM, Parg 50 uM, AG 1 uM | −15.7 | −22.2--9.1 | <0.01 | 0.77 | 0.69-0.87 | <0.01 |

Abbreviations: CI confidence interval; RR, relative risk.

In Table 2 (and FIG. 2C), absolute and relative effects for the percentage of mosquitos feeding compared to #11 (Control) are displayed. Group 8 experienced a 24.1% increase in feeding, group 2 experienced a 16.9% increase in feeding, and Group 16 experienced a 13.6% increase in feeding; all differences were statistically significant. In contrast Groups 22 and 21 had less feeding than control group B.

Group 16 was significantly better than control group B in terms of the percentage of mosquitos feeding and good-great feeding. Group 8 was also better than Control Group B in terms of the percent of mosquitos that fed, but only approached a statistically significant difference in terms of good-great feeding on the relative scale. Achieving statistical significance on the absolute scale may have occurred with a larger number of experiments. An additional five groups (Groups 18, 10, 17, 15, and 21) achieved significantly better results than Control Group B in terms of good-great feeding on the absolute and/or relative scales, but were not significantly different in the percentage of mosquitos that fed.

The present example sought to develop a solution that would be used not only to entice mosquito feeding, but provide a stable environment for DNA aptamer gold nanoparticle conjugates (Apt-AuNP) used to identify infection status in mosquitoes. Overall, the addition of small molecule drug compounds increased the feeding and engorgement rate of the diagnostic solution such that roughly double the number of mosquitoes captured may be able more easily assessed by eye for any sort of imbibed colorimetric assay, such as Apt-AuNP.

While not novel drugs, the panel of drugs for these neuromodulation studies of mosquito feeding behavior have never been used in this regard. Clonidine, an $\alpha_2$-adrenergic agonist has previously been used to treat hypertension (MacDougall 1970) and attention deficit hypersensitivity disorder (ADHD) (Ming 2011). Pargyline, a monoamine oxidase inhibitor, was previously used as an antihypertension treatment (Bryant 1961) but is no longer used. In addition to its action on TRPA1 receptors, polygodial has shown to be an inhibitor of mitochondrial ATP synthesis by affecting mitochondrial membrane potential, which may explain its antifungal properties (Castelli 2005). The inhibitory small peptide Antagonist G has previously found use in increasing receptor-mediated liposome uptake in small cell lung carcinoma models, thus increasing the uptake of encapsulated anti-cancer drugs (Moreira 2004).

Utilizing these drugs to increase engorgement can be used in trap-based insecticides, where perhaps an insufficient amount of kill agent is currently being imbibed.

Materials and Methods

Reagents: Sodium chloride, magnesium chloride, sodium bicarbonate, sucrose, and β,γ-methyleneadenosine 5'-triphosphate disodium salt were purchased from Sigma-Aldrich (St. Louis, MZ). Clonidine, pargyline, polygodial, TCB-2 and antagonist G were purchased from Tocris (Bristol, UK). Liver powder was purchased from MP Biomedical (Santa Ana, Calif.). Brewer's Yeast was purchased from Insect Sales (Washington, USA).

Mosquito rearing: *Aedes aegypti* eggs were sourced from the USDA-CMAVE and stored in a dark, humidified environment until use. New eggs were also generated in the Willenberg laboratory from adults generated from these eggs. Approximately 1,000 eggs were placed into three liters of deionized water with 12 ml of Brown Food (brewer's yeast and liver powder) and kept in a humidified incubator at 29° C. After 50% or more larvae had progressed to the pupal stage, the mosquitoes were transferred to emergence cups and placed inside an adult cage. Adults were maintained in a humidified incubator at 29° C., with a 12/12 hour light cycle and fed 10% sucrose ad libitum via a saturated cotton ball placed atop the cage.

Feeding studies: Feeding studies were carried out in specimen cups in groups of fifty 4-10 day old adult female *Ae. aegypti* mosquitoes. Mosquitoes were starved overnight prior to experimentation. To perform the experiment, a 1 cm square piece of gauze containing a feeding solution (10% sucrose, solution #11 or #11 laced with drugs) was placed atop the specimen cup's mesh lid. Mosquitoes were allowed to feed off the solution for one hour inside a humidified incubator at 29° C. At the end of the experiment, the gauze square was removed and the mosquitoes were immediately cold anaesthetized inside a 4° C. cold room. After cold anaesthetizing, mosquitoes were sorted for feeding based upon degrees of engorgement. A guide for feeding that was established in the PI's lab was used for determining engorgement. Drug descriptions are outlined in table 3 and their respective dosage and combinations for each experimental group are Table 4.

Statistical Analysis: Binomial regression with least squares means was used to calculate the percentage of mosquitos feeding and the percentage with good-great feeding according to each feeding group. Generalized estimating equations (GEEs) were used to account for the nonindependence (correlation) of mosquitos in each experimental unit (feeding cup). An exchangeable correlation structure was utilized for the analysis.

Binomial regression was also utilized to calculate both absolute and relative effects for differences in the percentage of mosquitos feeding and the percentage of mosquitos with good/great feeding compared to control group B. Significant ($p<0.05$), borderline significant ($p=0.05-0.06$), and marginally significant ($p=0.07-0.08$) effects are reported. Absolute differences in the percentage of mosquitos that fed and differences in the percentage of mosquitos with good/great feeding compared to control group B were the outcomes of primary interest with relative effects as secondary outcomes.

REFERENCES CITED 1. http://www.who.int/mediacentre/factsheets/fs117/en/as of Apr. 5, 2017
2. https://www.cdc.gov/zika/geo/united-states.html as of Mar. 30, 2017
3. Corfas R., Vosshall L. The Cation Channel TRPA1 Tunes Mosquito Thermotaxis to Host Temperatures, eLife (2015) 4:e11750.
4. Takken W, Knols B G Odor-Mediated Behavior of Afrotropical Malaria Mosquitoes, (1999) Annu. Rev. Entomol. 44:131-57
5. Sparks J T, Dickens J C, Mini Review: Gustatory Reception of Chemicals Affecting Host Feeding in Aedine Mosquitoes, Pesticide Biochemistry and Physiology (2016), http://dx.doi.org/10.1016/j.pestbp.2016.12.009
6. Liu, H et al. Functional analysis of Orco and odorant receptors in odor recognition in *Aedes albopictus*. Parasites & Vectors (2016) 9:363
7. Werner-Reiss, U. et al. Sensitivity of the Mosquito *Aedes Aegypti* (Culicidae) Labral Apical Chemoreceptors to Phagostimulants. Journal of Insect Physiology 45 (1999) 629-636
8. Siju K P, Reifenrath A, Scheiblich H, Neupert S, Predel R, Bill S. Hansson, Joachim Schachtner, Rickard Ignel. Neuropeptides in the Antennal Lobe of the Yellow Fever Mosquito, *Aedes aegypti*. The Journal of Comparative Neurology 2014 522:592-608
9. Harrington, L., Edman, J., Scott, T. Why Do Female *Aedes aegypti* (Diptera: Culicidae) Feed Preferentially and Frequently on Human Blood? Journal of Medical Entomology 2001, 38(3):411-422
10. Choo Y M, Buss G K, Tan K, Leal W S Multitasking roles of Mosquito labrum in oviposition and blood feeding. Front. Physiol 2015, 6:306.doi:10.3389/fphys.2015.00306
11. Jung et al. A novel olfactory pathway is essential for fast and efficient blood-feeding in mosquitoes. Scientific Reports 2015, 5:13444
12. Franz, A., Kantor, A., Passarelli, A. L., Clem, R. Tissue Barriers to Arbovirus Infection in Mosquitoes. Viruses 2015, 7, 3741-3767
13. Gwadz, R. Regulation of Blood Meal Size in the Mosquito. J. Insect Physiol., 1969, Vol. 15
14. Long, T., Murdock, L. Stimulation of blowfly feeding behavior by octopaminergic drugs. P Natl Acad Sci USA 1983, 80 (13) 4159-4163
15. Dolzer, J., Krannich, S., Fischer, K., Stengl, M. Oscillations of the Transepithelial Potential of Moth Olfactory Sensilla are Influenced by Octopamine and Serotonin. The Journal of Experimental Biology 2001. 204, 2781-2794
16. Siju, K P., Hansson, B., Ignell, R. Immunocytochemical Localization of Serotonin in the Central and Peripheral Chemosensory System of Mosquitoes. Arthropod Structure & Development. 2008. 248e259
17. El-Kholy, S., Stephano, F., Li, Y., Bhandari, A., Fink, C., Roeder, T. Expression analysis of octopamine and tyramine receptors in *Drosophila*. Cell Tissue Res. 2015. 361:669-684
18. Zhou, C., Rao, Y., Rao, Y. A Subset of Octopaminergic Neurons are Important for *Drosophila* Aggression. Nature Neuroscience. 2008. doi:10.1038/nn.2164
19. Farooqui, T., Robinson, K., Vaessin, H., Smith, B. Modulation of Early Olfactory Processing by an Octopaminergic Reinforcement Pathway in the Honeybee. The Journal of Neuroscience, 2003. 23(12):5370-5380
20. Vleugels, R., Verlinden, H., Vanden Broeck, J. Serotonin, Serotonin Receptors and Their Actions in Insects. Neurotransmitter. 2015. 2: e314. doi: 10.14800/nt.314
21. Gasque, G., Conway, S., Huang, J., Rao, Y., Vosshall, L. Small Molecule Drug Screening in *Drosophila* Identifies the 5HT2A Receptor as a Feeding Modulation Target. Scientific Reports. 2013.DOI: 10.1038/5rep02120
22. Fox, M., French, H., LaPorte, J., Blackler, A., Murphy, D. The Serotonin 5-HT2A Receptor Agonist TCB-2: A Behavioral and Neurophysiological Analysis. Psychopharmacology. 2010. 212:13-23
23. Radford, J., Davies, S., Dow, J. Systematic G-protein-coupled Receptor Analysis in *Drosophila melanogaster* Identifies a Leucokinin Receptor with Novel Roles. The Journal of Biological Chemistry. 2002. DOI 10.1074/jbc.M203694200
24. Al-Anzi, B. et al. The Leucokinin Pathway and its Neurons Regulate Meal Size in *Drosophila*. Curr Biol. 2010. 20(11): 969-978. doi:10.1016
25. Kwona, H., Ali Aghab, M., Smith, R., Nachmand, R., Marion-Pollb, F., Pietrantonioa, P. Leucokinin Mimetic Elicits Aversive Behavior in Mosquito *Aedes Aegypti* (L.) and Inhibits the Sugar Taste Neuron. P Natl Acad Sci. 2016. DOI: 10.1073
26. Woll, P., Rozengurt, E. A Neuropeptide Antagonist That Inhibits the Growth of Small Cell Lung Cancer in Vitro. Cancer Research. 1990. 50, 3968-3973.
27. Clements, A N., Chapman and Hall. The Biology of Mosquitoes, Vol. I; Development, Nutrition and Reproduction. 1992. ISBN 0 412 40180 0

28. Romeo, J. Phytochemicals in Human Health Protection, Nutrition, and Plant Defense. 1999. ISBN 978-1-4615-4689-4

29. Galizia C G, Sachse S. Odor Coding in Insects. In: Menini A, editor. The Neurobiology of Olfaction. Boca Raton (Fla.): CRC Press/Taylor & Francis; 2010. Chapter 2. Available from: https://www.ncbi.nlm.nih.gov/books/NBK55975//

30. Macdougall, G. J. Addis, N. Mackay, I. W. Dymock, A. G. G. Turpie, D. L. K. Ballingall, W. J. Maclennan, B. Whiting, J. G. Macarthur. Treatment of Hypertension with Clonidine. *British Medical_Journal,* 1970, 3, 440-442.

31. Ming, X., Mulvey, M., Mohanty, S., Patey, V. Safety and Efficacy of Clonidine and Clonidine Extended-Release in the Treatment of Children and Adolescents with Attention Deficit and Hyperactivity Disorders. *Adolescent Health, Medicine and Therapeutics.* 2011:2 105-112.

32. Bryant, J M., Torosdag, S., Schvartz, N., Lucian, F., Fertig, H., Schwartz, S., Quan, R B F. Antihypertensive Properties of Pargyline Hydrochloride. *J.A.M A.,* 1961, 178:406-9.

33. Castelli, M V., Lodeyro, A F., Malheiros, A., Zacchino, S A S., Roveri, O A. Inhibition of the Mitochondrial ATP synthesis by Polygodial, a Naturally Occurring Dialdehyde Unsaturated Sesquiterpene. *Biochemical Pharmacology.* 2005. 70 82-89.

34. Moreira, J N., Gaspar, R. Antagonist G-Mediated Targeting and Cytotoxicity of Liposomal Doxorubicin in NCI-H82 Variant Small Cell Lung Cancer. *Brazilian Journal of Medical and Biological Research.* 2004. 37: 1185-1192.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A composition comprising:

(a) a mosquito food source, wherein the mosquito food source is sucrose; and (b) a mosquito neuromodulation agent;

wherein the mosquito neuromodulation agent enhances mosquito feeding in comparison to a control composition without the mosquito neuromodulation agent; and wherein the mosquito neuromodulation agent is selected from TCB-2, polygodial, antagonist G, or a combination thereof.

2. The composition of claim 1, wherein the sucrose is present at about 10% sucrose.

3. The composition of claim 1, further comprising 15 mM NaCl, 1 mM $NaHCO_3$, 1 μM $MgCl_2$, 5 μM β,γ-methyleneadenosine 5'-triphosphate disodium salt (β,γ-met ATP), or a combination thereof.

4. The composition of claim 1, wherein the mosquito neuromodulation agent comprises TCB-2.

5. The composition of claim 1, wherein the mosquito neuromodulation agent comprises polygodial.

6. The composition of claim 1, wherein the mosquito neuromodulation agent comprises antagonist G.

7. A method for enhancing mosquito feeding, comprising:

(a) providing a payload reservoir containing a composition, wherein the composition comprises:

a mosquito food source, wherein the mosquito food source is sucrose; and a mosquito neuromodulation agent; and (b) allowing mosquitoes to alight on or feed on the payload reservoir;

wherein the mosquito neuromodulation agent enhances mosquito feeding in comparison to a control composition without the mosquito neuromodulation agent; and wherein the mosquito neuromodulation agent is selected from TCB-2, polygodial, antagonist G, or a combination thereof.

8. The method of claim 7, wherein the sucrose is present at about 10% sucrose.

9. The method of claim 7, wherein the composition further comprises 15 mM NaCl, 1 mM $NaHCO_3$, 1 μM $MgCl_2$, 5 μM β,γ-methyleneadenosine 5'-triphosphate disodium salt (β,γ-met ATP), or a combination thereof.

10. The method of claim 7, wherein the composition further comprises a detector conjugate, wherein the detector conjugate comprises a gold nanoparticle conjugated to a specific detector molecule.

11. The method of claim 7, wherein the mosquito neuromodulation agent enhances mosquito feeding by at least 10%.

12. The method of claim 7, wherein the mosquitoes are *Aedes aegypti.*

13. The composition of claim 1, wherein the mosquito neuromodulation agent enhances mosquito feeding by at least 10%.

14. The method of claim 7, wherein the mosquito neuromodulation agent comprises TCB-2.

15. The method of claim 7, wherein the mosquito neuromodulation agent comprises polygodial.

16. The method of claim 7, wherein the mosquito neuromodulation agent comprises antagonist G.

17. The composition of claim 1, wherein the composition further comprises a detector conjugate, wherein the detector conjugate comprises a gold nanoparticle conjugated to a specific detector molecule.

* * * * *